US008609368B2

(12) United States Patent
Cho et al.

(10) Patent No.: US 8,609,368 B2
(45) Date of Patent: Dec. 17, 2013

(54) PROCESS FOR PURIFYING VANCOMYCIN WET BODY

(75) Inventors: Jin Suk Cho, Daejeon (KR); Jong Won Yoon, Daejeon (KR); Eun Soo Choi, Daejeon (KR); Jeong Min Kim, Daejeon (KR); Ho Joon Choi, Daejeon (KR); Sung Hag Kim, Suwon-si (KR); Seong Kyu Kim, Daejeon (KR); Jae Jong Kim, Daejeon (KR)

(73) Assignees: Genotech Co., Ltd., Daejeon (KR); Samyang Biopharmaceuticals Corporation, Seoul (KR)

( * ) Notice: Subject to any disclaimer, the term of this patent is extended or adjusted under 35 U.S.C. 154(b) by 0 days.

(21) Appl. No.: 13/144,285

(22) PCT Filed: Nov. 26, 2009

(86) PCT No.: PCT/KR2009/007022
§ 371 (c)(1),
(2), (4) Date: Jul. 12, 2011

(87) PCT Pub. No.: WO2010/082726
PCT Pub. Date: Jul. 22, 2010

(65) Prior Publication Data
US 2011/0275786 A1    Nov. 10, 2011

(30) Foreign Application Priority Data
Jan. 13, 2009    (KR) .................. 10-2009-0002698

(51) Int. Cl.
*C12P 1/00*    (2006.01)
*A61K 38/14*    (2006.01)

(52) U.S. Cl.
USPC .............................................. 435/41; 530/322

(58) Field of Classification Search
None
See application file for complete search history.

(56) References Cited

U.S. PATENT DOCUMENTS

| 3,067,099 | A | | 12/1962 | McCormick et al. |
| 4,885,275 | A | * | 12/1989 | Robison .................. 514/2.7 |
| 5,149,784 | A | * | 9/1992 | Chu ....................... 530/344 |
| 5,223,413 | A | | 6/1993 | Nagy et al. |
| 5,235,037 | A | | 8/1993 | Krishnan |
| 5,574,135 | A | | 11/1996 | Chu |
| 5,616,595 | A | | 4/1997 | Chu et al. |
| 5,853,720 | A | | 12/1998 | Pflaum et al. |
| 7,018,814 | B2 | | 3/2006 | Lee et al. |
| 2006/0003406 | A1 | | 1/2006 | Lee et al. |
| 2010/0228005 | A1 | | 9/2010 | De Tommaso |

FOREIGN PATENT DOCUMENTS

| CN | 1857716 A | 11/2006 |
| CN | 101341167 A | 1/2009 |
| EP | 0 455 772 | 11/1991 |
| KR | 1998-39737 A | 8/1998 |
| WO | WO 96/24615 A1 | 8/1996 |
| WO | WO 2007/068644 A1 | 6/2007 |

OTHER PUBLICATIONS

Williams et al., "The Lyophilization of Pharmaceuticals: A Literature Review", Journal of Parenteral Science and Technology, Vo. 28, No. 2, pp. 48-59.*
Williams et al., "The Lyophilization of Pharmaceuticals: A Literature Review", Journal of Parenteral Science and Technology, 1984, vol. 28, No. 2, pp. 48-59.*
PCT International Search Report for PCT Counterpart Application No. PCT/KR2009/007022, 2 pgs (Jul. 26, 2010).
Written Opinion of the International Search Authority for PCT Counterpart Application No. PCT/SG2009/007022, 3 pgs (May 4, 2010).
Chinese Office Action, Application No. 200980154447.1, dated Jan. 29, 2013, 11 pages.

* cited by examiner

*Primary Examiner* — Suzanne M Noakes
(74) *Attorney, Agent, or Firm* — Blakely, Sokoloff, Taylor & Zafman LLP

(57) ABSTRACT

Provided is a process for purifying a vancomycin wet body, comprising: dissolving a wet body obtained from a microorganism-fermented solution containing vancomycin into a water soluble solvent to a concentration of about 1 to 40 g/L and carrying out reverse osmosis filtration; and carrying out lyophilization of the filtered vancomycin. The process for purifying a vancomycin wet body provides high-purity vancomycin, while avoiding degradation of stability during a drying step.

7 Claims, 3 Drawing Sheets a.

b.

c.

Results of Reverse Osmosis Filtration and Lyophilization

A: Wet body (Before Spray Drying)
B: Spray Drying
C: Vacuum Drying (12 hr)
D: Vacuum Drying (36 hr)
E: Vacuum Drying (48 hr)

PROCESS FOR PURIFYING VANCOMYCIN WET BODY

CROSS-REFERENCE TO RELATED APPLICATIONS

This patent application is a U.S. National Phase application under 35 U.S.C. §371 of International Application No. PCT/KR2009/007022, filed Nov. 26, 2009, entitled PROCESS FOR PURIFYING VANCOMYCIN WET BODY, which claims priority to Korean patent application number 10-2009-0002698, filed Jan. 13, 2009.

TECHNICAL FIELD

The present invention relates to a process for purifying a vancomycin wet body using reverse osmosis. More particularly, the present invention relates to a process for purifying a vancomycin wet body, which can prevent a drop in purity caused by poor temperature stability during a drying step in a process for preparing vancomycin.

BACKGROUND ART

Vancomycin is represented by the following Chemical Formula I and is produced by Actinomycetes microorganisms, i.e., *Amycolatopsis orienatalis* (ATCC 19795) strains. Vancomycin is also prepared by chemical bonding of —O-vancosamin- —O-glucosyl with a heptapeptide. In addition, vancomycin is a glycopeptide-type antibiotic having a molecular weight of about 1449, and realizes antibiotic activity by the mechanism in which it is bound to a mucopeptide precursor terminated with D-ala-D-ala to inhibit cell wall synthesis. Generally, vancomycin shows an excellent pharmacological effect against gram-positive bacteria, such as Streptococci, Staphylococci and *Clostridium difficile*, and penicillin- or cephalosporin antibiotic-resistant gram-positive bacteria.

In addition, it is known that vancomycin is highly effective in the treatment against methicillin-resistant staphylococcus aureus (MRSA) fatal to patients subjected to surgery, old-aged patients and persons with weak immunity. Such vancomycin salts, particularly, vancomycin hydrochloride has been currently used as oral (liquid or capsules) or injection formulations.

Various technological processes for separating and purifying vancomycin have been known to date, and typical examples thereof are as follows:

U.S. Pat. No. 7,018,814 and Korean Patent No. 554481 disclose a method for purifying vancomycin hydrochloride, including: (a) passing a microorganism-fermented solution containing vancomycin through a strong acidic cation exchange resin under the condition of pH 1-3 by using, as an eluent, an aqueous ammonium hydroxide solution having a concentration of 0.05-0.2N and a pH of 9-11; (b) adjusting the resultant solution to a pH of 3-5 and passing it continuously through a weak basic anion exchange resin and alumina, followed by washing with water, to remove the pigments; (c) passing the resultant solution through a hydrophobic adsorption resin by using, as an eluent, an aqueous C1-C4 alcohol solution; and (d) adding hydrochloric acid to the resultant solution to adjust the pH to 2-5, and adding a water-soluble organic solvent containing a C1-C4 alcohol, acetonitrile, acetone or methyl isobutyl ketone to perform crystallization of vancomycin hydrochloride.

According to the above patents, it is said that crystal bodies are obtained through the crystallization step during the separation and purification of the vancomycin-containing microorganism-fermented solution, the crystal bodies are filtered, and the filtered precipitate (crystal bodies) are subjected to vacuum drying (vacuum drying at a temperature of 40° C. or lower in examples) in order to obtain vancomycin hydrochloride.

U.S. Pat. No. 5,853,720 discloses a process for purifying vancomycin, including subjecting a microorganism-fer-

[Chemical Formula I]

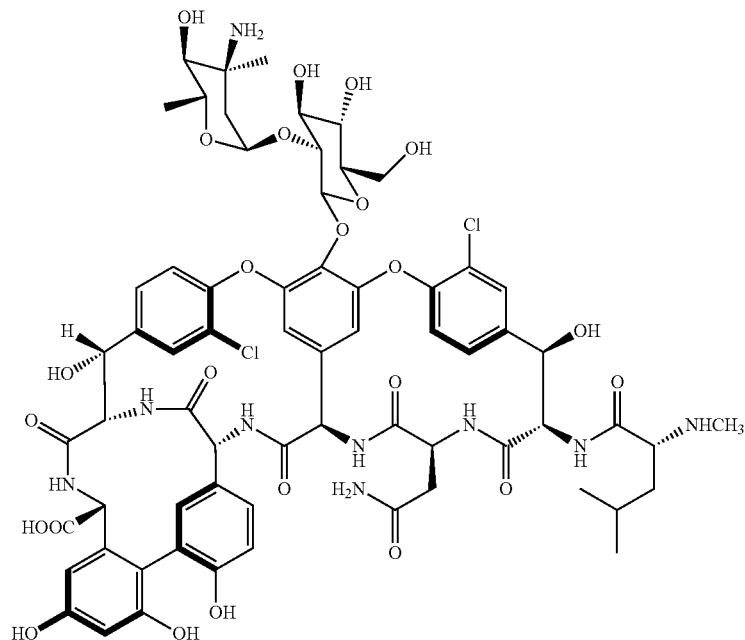

mented solution to preparative chromatography using a silica column, and carrying out precipitation by using ethanol from a salt-water-ethanol solution. According to the above patent, a main fraction (average purity: 93%) and a side fraction (purity of 90% or less) are obtained from the silica gel column after the cultivation-precision filtration-adsorption using an ion exchange resin. In the case of the main fraction, concentration-filtration-concentration and discoloration are performed, and then high-temperature spray drying (air inlet temperature: 115-130° C., air outlet temperature: 85±5° C.)—vacuum drying (45-50° C.) are carried out to obtain a dried solid product. On the other hand, in the case of the side fraction, desalting and concentration using a reverse osmosis process after acidification—precipitation (crystallization) using ethanol after adding ethanol and sodium chloride—cooling and filtration are carried out, and then the resultant product is resent to the silica gel column to perform the treatment for the main fraction. In the case of the above purification process, a relatively large number of steps (at least 7 to 11 steps) are included. Although the above patent describes about the purity of vancomycin (salt) obtained after the treatment with the silica gel column, there is no description about a change in purity after the subsequent steps (particularly, reverse osmosis filtration step and vacuum drying step). As described hereinafter, although vancomycin with a purity of 93% or higher can be obtained by the above process, the purity decreases in the subsequent drying steps (particularly, high-temperature spray drying and vacuum drying at 45-50° C.), thereby making it difficult to obtain a product having a purity satisfying the criteria defined by European Pharmaceutical Standards, i.e., a purity of 93% or higher.

However, the above-mentioned processes according to the related art cause such problems as degradation of purity of at least 3.2% and at most 5.6% for 1-2 days of vacuum drying and degradation of stability of vancomycin. In addition, when the vacuum drying step is performed at a decreased temperature of 25° C. for the same period of time, it is shown that a change in purity is merely less than 1%, however, the resultant product contains impurities including at least 0.5% of ethanol and up to 4-10% of moisture.

As described above, vancomycin is a temperature-sensitive medicine, and thus a vacuum drying temperature of 40-50° C. cannot ensure the stability in terms of purity. On the other hand, a vacuum drying temperature decreased to 40° C. or less cannot satisfy the standards of ethanol content and moisture content. Therefore, such vacuum drying adopted as the final step for providing a dried product in the conventional purification processes is not suitable for the efficient production of stable high-purity vancomycin. Moreover, the above patents according to the related art are focused on the separation and purification processes, and there is no particular description about the problems of degradation of stability and purity caused by the drying step.

Meanwhile, according to the European Pharmaceutical Standards (European Pharmacopoeia 6.0), particularly for stable high-purity vancomycin, it is required for vancomycin to have a purity of 93% or higher and a moisture content of at most 5%. It is also required for vancomycin to have an ethanol content less than about 0.5% with reference to ICH Harmonised tripartite guideline (Impurities: Guideline for Residual Solvents). Under these circumstances, there is an imminent need for developing a process for purifying vancomycin, which prevents a drop in purity caused by poor temperature stability and satisfies various standards related to medicines.

SUMMARY

We have conducted many studies to overcome the above-mentioned problems occurring in the prior art. As a result, we have developed a process for preparing high-purity vancomycin by subjecting a vancomycin wet body, obtained in a process for purifying vancomycin (more particularly, vancomycin salts such as vancomycin hydrochloride) from a microorganism-fermented solution containing vancomycin, to concentration via reverse osmosis filtration and lyophilization so as to ensure stability during the drying step.

Therefore, it is an object of the present invention to provide a process for purifying a vancomycin wet body that can prevent a drop in purity caused by degradation of stability during a drying step in a vancomycin purification process.

It is another object of the present invention to provide a process for purifying vancomycin wet body that can satisfy various criteria required in European Pharmaceutical Standards, etc.

In one aspect, it is provided a process for purifying a vancomycin wet body, comprising the steps of:

a) dissolving a wet body obtained from a microorganism-fermented solution containing vancomycin into a water soluble solvent to a concentration of about 1 to 40 g/L and carrying out reverse osmosis filtration; and b) carrying out lyophilization of the filtered vancomycin.

The process for purifying a vancomycin wet body disclosed herein solves the problem related to degradation of stability occurring in a drying step of conventional vancomycin purification processes, thereby providing vancomycin with high purity. Therefore, it is expected that the process has high industrial applicability.

BRIEF DESCRIPTION OF DRAWINGS

The above and other aspects, features and advantages of the present invention will be more apparent from the following detailed description taken in conjunction with the accompanying drawings in which.

DETAILED DESCRIPTION

Figure 1:
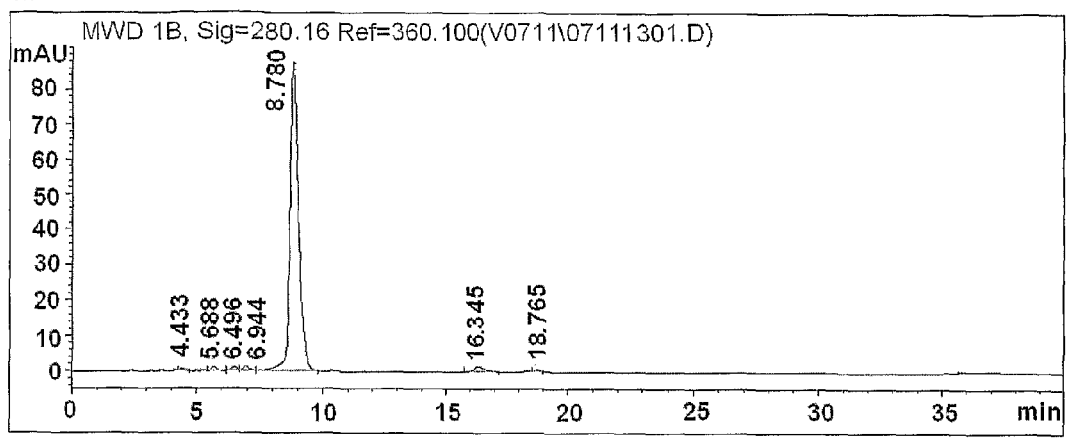
FIG. 1a, FIG. 1b, and FIG. 1c show the results of HPLC analysis for a wet body, a concentrate obtained after reverse osmosis filtration and a lyophilized product, each illustrating a change in purity during the purification process of a vancomycin-containing wet body according to Example 1.
Figure 1:
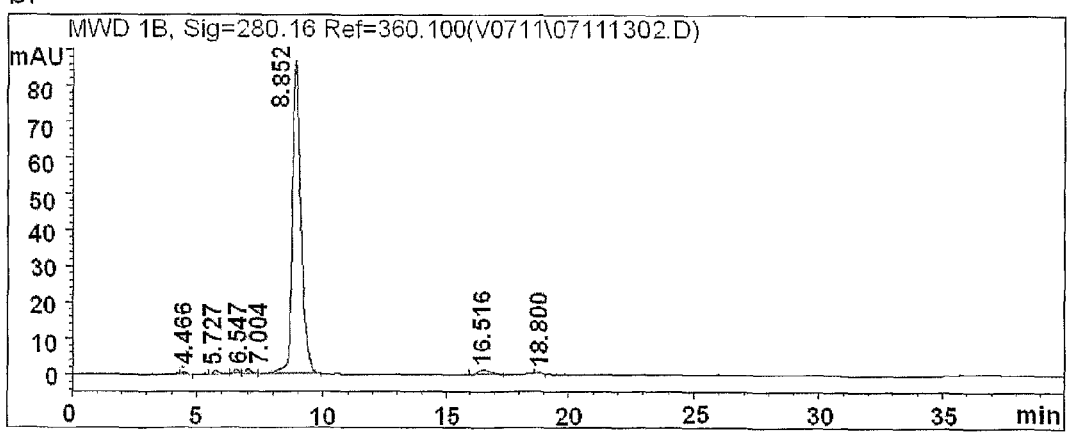
Figure 1:
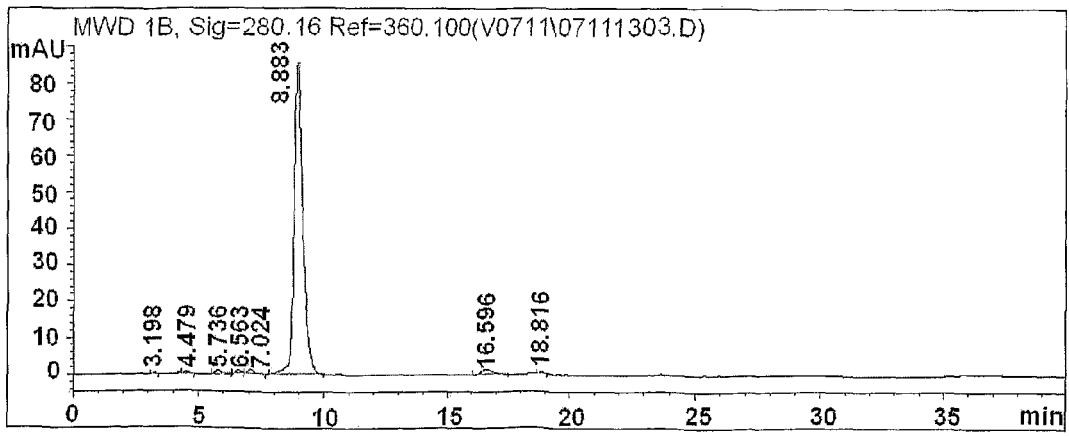

Exemplary embodiments now will be described more fully hereinafter. The present invention, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art.

As used herein, the term 'microorganism' in the expression of a microorganism-fermented solution containing vancomycin is not limited to a particular species but refers to microorganisms capable of producing vancomycin and accumulating vancomycin in their culture. Particular examples of such microorganisms are described in U.S. Pat. Nos. 3,067,099 and 5,235,037 and Korean Patent No. 554481, the teachings of which are incorporated herein by reference in their entirety.

For example, as described above, the microorganism-fermented solution containing vancomycin may be obtained by culturing (or shaking culturing) *Amycolatopsis orientalis*, particularly *Amycolatopsis orientalis* (ATT 19795) or *Norcardia orientalis*, particularly *Nocardia orientalis* NRRL 2452.

The process in accordance with the present invention is carried out for purifying a wet body obtained from a microorganism-fermented solution containing vancomycin.

As used herein, the term 'wet body' refers to vancomycin still containing moisture after it is obtained from a microorganism-fermented solution containing vancomycin. Herein, the wet body has a moisture content of about 10-99% (w/v), preferably about 30-50% (w/v). Typically, the term wet body may refer to a non-dried crystal body obtained by crystallization (particularly, crystallization in ethanol) during or after purification, and by filtration, wherein the crystal body is separated from a crystallization solution mixed with a water soluble organic solvent. In addition, the wet body includes vancomycin having a purity of about 93% or higher, preferably about 95% or higher, and a solid content of about 10-90%, preferably about 50-70%.

As mentioned above, conventional separation-purification processes including chromatography, crystallization, etc. (typically, separation processes based on crystallization) may be used to obtain a wet body from a microorganism-fermented solution containing vancomycin. Particularly, as described in Korean Patent Laid-Open No. 1998-39737A, the microorganism-fermented solution containing vancomycin is separated and purified in a multi-step manner, followed by concentration and crystallization in ethanol, to obtain the wet body. More particularly, the microorganism-fermented solution containing vancomycin is separated and purified in a multi-step manner, concentrated to a concentration of about 150-200 g/L, and ethanol is introduced thereto under the conditions of a conductivity of about 15-25 ms/cm and pH of about 2-4 at a volume ratio of about 1.5-2 to perform crystallization in ethanol. In this manner, it is possible to obtain the wet body.

In addition, as described in Korean Patent No. 554481, a microorganism-fermented solution containing vancomycin may be separated and purified by being passed sequentially through a strong acidic cation exchange resin, weak basic anion exchange resin, alumina and hydrophobic adsorptive resin to obtain the wet body. The teachings of the above publications are incorporated herein by reference in their entirety.

Reverse Osmosis Filtration

According to one embodiment of the present invention, the wet body is dissolved first into a water soluble solvent to a concentration of about 1 to 40 g/L, preferably about 15-30 g/L. Herein, particular examples of the water soluble solvent may include water, C1-C4 aliphatic alcohols (e.g. methanol, ethanol, isopropanol, etc.) or mixtures thereof, preferably water, and more preferably purified water. If the wet body concentration in the water soluble solvent is too high, dissolution of the wet body requires an excessively long time due to the organic solvent, such as ethanol, contained in the wet body. Particularly, if the ethanol content is higher than the water content, the wet body cannot be dissolved completely, so that pre-filtration carried out before the reverse osmosis filtration is relatively complicated and the non-dissolved vancomycin causes a drop in yield. On the other hand, if the wet body concentration is too low, dissolution of the wet body is performed easily regardless of the ethanol content. However, in this case, pre-filtration and reverse osmosis filtration require an increased time, resulting in degradation of the overall efficiency. Therefore, it is preferred to control the wet body concentration in the water soluble solvent to the above-defined range.

As described above, after the wet body is dissolved into the water soluble solvent to an adequate concentration, the impurities in the wet body are removed and vancomycin is concentrated by using the reverse osmosis step (filtration). According to a preferred embodiment, pre-filtration is performed before the reverse osmosis filtration, and the pre-filtration preferably uses a sterilized filter with a pore size of about 0.1-0.6 μm, typically about 0.45 μm. Such pre-filtration is performed before the reverse osmosis filtration, because it facilitates the reverse osmosis filtration by removing non-dissolved impurities and provides sterilized vancomycin.

The reverse osmosis step, i.e., reverse osmosis filtration is carried out to remove salts, such as ammonium chloride, sodium chloride or potassium chloride, or organic solvents, such as aliphatic alcohols, from a mixture of water and C1-C4 aliphatic alcohols. The filter membrane that may be used for the reverse osmosis filtration is generally made of polyamide, polysulfone, polypropylene, urethane, or the like. The membrane preferably has a cut-off molecular weight of about 100-500, and more preferably about 200-400. If the filtration membrane has an excessively low cut-off molecular weight, filtration using the same membrane requires a long time and increases the operational pressure, making it difficult to separate vancomycin. On the other hand, if the filtration membrane has an excessively high cut-off molecular weight, the filtration using the same membrane provides a decreased yield of vancomycin or vancomycin salts. Therefore, it is preferred to use a filter membrane having the above-defined range of cut-off molecular weights. Typical examples of such filter membranes may include Nanomax™ 50 RO Spiral cartridge (available from Millipore Corporation), TFC-SR100-T (KOCK membrane system), or the like.

Preferred operational conditions of the reverse osmosis filtration membrane and system are described in the following Table 1, but the scope of the present invention is not limited thereto.

TABLE 1

| Area of membrane (m²) | Injection space (mm) | Operational pressure (bar) | Operational Temperature (° C.) | Cleaning temperature (° C.) | Acceptable range of pH |
|---|---|---|---|---|---|
| 1.7-2.5 | 0.7-1.2 | 4.8-31.0 | 5-50 | 35-50 | 2-11 |

In addition, particular examples of the organic solvents and salts applicable to the reverse osmosis filtration membrane and system are described in the following Table 2.

TABLE 2

| Organic solvents and salts | Maximum concentration (%)* |
|---|---|
| Caustic soda | 10.5 |
| Hydrogen peroxide | 0.25 |
| Ethanol | 96 |
| Methanol | 50 |
| Sulfuric acid | 2 |
| Phosphoric acid | 2 |
| Acetic acid | 5 |
| Oxalic acid | 5 |
| Citric acid | 5 |
| Ethylene glycol | 60 |
| Glycerin | 100 |
| Acetone | 5 |
| Methyl ethyl ketone | 5 |

TABLE 2-continued

| Organic solvents and salts | Maximum concentration (%)* |
|---|---|
| Tetrahydrofuran | 5 |
| Dioxane | 5 |
| DMF (Dimethylformamide) | 5 |
| DMSO (Dimethyl sulfoxide) | 5 |
| Hydrochloric acid | 2 |
| Ammonia | 10.5 |
| IPA (isopropyl alcohol) | 90 |
| Butanol | 90 |

*% Concentration to water

According to a preferred embodiment of the present invention, vancomycin is concentrated to a concentration of about 50-200 g/L, preferably about 120-180 g/L, through the reverse osmosis filtration. After the concentration, an excessively high concentration causes easy precipitation, thereby increasing the turbidity and reducing the purity. On the other hand, an excessively low concentration causes an increase in volume of the sample to be lyophilized. Thus, it takes a long time to perform lyophilization of the sample. Moreover, such an excessively low concentration results in a low yield and low efficiency. Therefore, it is preferred to adjust the reverse osmosis filtration so as to provide the above-defined range of concentrations. It is also preferred to control the ethanol content to less than about 0.5% (w/v), more preferably about 0.1-0.3% (w/v). This is because an excessively low ethanol content causes an increase in time required for the reverse osmosis filtration in order to increase the removal of ethanol, resulting in degradation of the efficiency, while an excessively high ethanol content causes an increase in time in order to reduce the water content during the lyophilization, resulting in degradation of the efficiency.

According to the present invention, the vancomycin concentrated after the reverse osmosis filtration has a purity (preferably, about 95% or higher) similar to the purity of the wet body. Moreover, the loss of vancomycin in the filtrate during the filtration is less than about 1%.

Lyophilization

Then, the vancomycin concentrated through the reverse osmosis filtration is subjected to lyophilization. The term lyophilization is generally known to as a drying process in which a material is frozen, and the partial pressure of water vapor is reduced to perform sublimation of solid water into gas. The water having the shape of ice is not converted into liquid in the presence of heat energy supply but is sublimed into water vapor by reducing the partial pressure. According to the present invention, while the purity of the vancomycin concentrated during the lyophilization is maintained substantially (preferably, a change in purity of less than about 1%) at about 93% or higher, preferably about 95% or higher, the ethanol content is reduced to less than about 0.5% (w/v), preferably less than about 0.3% (w/v), and the water content is reduced to less than about 5% (w/v), preferably less than about 4% (w/v), and more preferably less than about 3%.

According to a preferred embodiment of the lyophilization step in the present invention, the concentrated vancomycin is lyophilized at about −4 to −196° C., preferably about −40 to −150° C., and more preferably at about −70° C. for about 3-48 hours, preferably about 12-36 hours. Then, the lyophilization system is driven gradually elevating the temperature of the system from about −60° C. up to about 40° C., preferably from about −40° C. up to about 20° C., for about 12-48 hours, preferably about 24-36 hours.

After that, the above condition is maintained for about 6-24 hours, preferably about 12-18 hours.

In this context, it is to be noted that it is possible to maintain the purity of high-purity vancomycin stably and to satisfy various standards about ethanol and water contents by using the lyophilization instead of the conventional drying steps used in the prior art, particularly spray drying and/or vacuum drying.

Mode for the Invention

Hereinafter, the present invention will be explained in more detail with reference to the examples. The following examples are for illustrative purposes only and not intended to limit the scope of this disclosure.

In the following examples, the system with the options as described hereinafter is used.

HPLC: Agilent Technologies
Column: ODS (C18), 4.6×250, 5 mm
Analysis Conditions
1. pH 3.2 TEA buffer: 4 ml of TEA (triethylamine) is introduced into 1996 ml of water and the pH is adjusted to 3.2 with phosphoric acid.
2. Mobile phase
   Mobile phase A: a mixed solution of pH 3.2 TEA buffer 920 ml, ACN (acetonitrile) 70 ml, and THF (tetrahydrofuran) 10 ml
   Mobile phase B: a mixed solution of pH 3.2 TEA buffer 700 ml, ACN 290 ml, and THF 10 ml
3. Gradient elution is carried out in the manner as described in the following Table 3.

TABLE 3

| Time (min) | Mobile phase A | Mobile phase B |
|---|---|---|
| 0-13 | 100 | 0 |
| 13-22 | 100→0 | 0→100 |
| 22-26 | 0 | 100 |

4. Flow rate: 1 ml/min.
5. Absorbance: 280 nm
6. Injection volume: 20 ml

PREPARATION EXAMPLE 1

Collection of Wet Body (1) from Microorganism-Fermented Solution Containing Vancomycin As described in Korean Patent Laid-Open No. 1998-39737A, a microorganism-fermented solution containing vancomycin is separated and purified in a multi-step manner to concentrate vancomycin to a concentration of 180 g/L, ammonium chloride is added thereto to adjust the conductivity to 21 ms/cm, and HCl is further added thereto to adjust the pH to 2.8. Under these conditions, ethanol is introduced at a volume ratio of 1.8 to perform crystallization in ethanol, thereby providing a wet body. The wet body has a purity of 96.6%, a solid content of 54%, and an ethanol and moisture content of 45%.

PREPARATION EXAMPLE 2

Collection of Wet Body (2) from Microorganism-Fermented Solution Containing Vancomycin As described in Korean Patent Laid-Open No. 1998-39737A, a microorganism-fermented solution containing vancomycin is separated and purified in a multi-step manner to concentrate vancomycin to a concentration of 176 g/L, ammonium chloride is added thereto to adjust the conductivity to 23 ms/cm, and HCl is further added thereto to adjust the pH to 2.5. Under these conditions, ethanol is introduced at a volume ratio of 1.8 to perform crystallization in ethanol, thereby providing a wet body. The wet body has a purity of 96.2%, a solid content of 55%, and an ethanol and moisture content of 40%.

PREPARATION EXAMPLE 3

Collection of Wet Body (3) from Microorganism-Fermented Solution Containing Vancomycin As described in Korean Patent Laid-Open No. 1998-39737A, a microorganism-fermented solution containing vancomycin is separated and purified in a multi-step manner to concentrate vancomycin to a concentration of 190 g/L, ammonium chloride is added thereto to adjust the conductivity to 20 ms/cm, and HCl is further added thereto to adjust the pH to 2.2. Under these conditions, ethanol is introduced at a volume ratio of 1.8 to perform crystallization in ethanol, thereby providing a wet body. The wet body has a purity of 95.8%, a solid content of 51%, and an ethanol and moisture content of 50%.

PREPARATION EXAMPLE 4

Collection of Wet Body (4) from Microorganism-Fermented Solution Containing Vancomycin As described in Korean Patent Laid-Open No. 1998-39737A, a microorganism-fermented solution containing vancomycin is separated and purified in a multi-step manner to concentrate vancomycin to a concentration of 175 g/L, ammonium chloride is added thereto to adjust the conductivity to 22 ms/cm, and HCl is further added thereto to adjust the pH to 2.5. Under these conditions, ethanol is introduced at a volume ratio of 1.8 to perform crystallization in ethanol, thereby providing a wet body. The wet body has a purity of 96.2%, a solid content of 42%, and an ethanol and moisture content of 55%.

EXAMPLE 1

Reverse Osmosis Filtration

First, 190 g of the wet body obtained according to Preparation Example 1 is dissolved into 2 L of purified water, and then filtered through a 0.45 μm sterilized filter system (available from Whatman Ltd., made of cellulose nitrate, product name: disposable filter funnel). Next, purified water is added thereto to a final solution volume of 4 L. Next, the resultant solution is introduced into the sample inlet of a reverse osmosis system (available from Millipore Corporation, product name: Helicon reverse osmosis system, membrane: Nanomax™ 50 membrane), and then concentrated while maintaining the pressure at 8 bars. After the solution is concentrated until about 3 L of filtrate is obtained through the revere osmosis filtration, 2 L of purified water is added. Next, the solution is further concentrated by applying the same pressure until 2 L of filtrate is obtained, 2 L of purified water is further added to, and the solution is further concentrated to a final volume of about 0.5 L. Then, the system is depressurized and the resultant concentrate is recovered for 10 minutes.

After analyzing the recovered concentrate, it is shown that vancomycin has a purity of 96.4%, a concentration of 118 g/L and an ethanol content of 0.38% (w/v).

Lyophilization

The vancomycin concentrate having a concentration of 118 g/L is poured into a container made of iron to a level of 1 cm of lower, and lyophilized completely at −70° C. for 1 day. Next, the iron container containing the lyophilized concentrate is introduced into a lyophilization system (available from Labconco, product name: Freeze dry system), the shelf temperature of which is controlled to −40° C., and lyophilized for 42 hours. The lyophilized vancomycin is analyzed.

It is shown from the analysis that there is no change in vancomycin purity (96.4%) 24 hours after the lyophilization, and the ethanol content and the moisture content are 0.25% (w/v) and 3.4% (w/v), respectively.

In this example, HPLC analysis is carried out in order to observe variations in purity during the purification of vancomycin from the wet body. The results are shown in FIGS. 1a-1c.

As can be seen from FIGS. 1a-1c, there is no substantial change in peak area corresponding to vancomycin among the wet body (FIG. 1a), the concentrate (FIG. 1b) obtained after the reverse osmosis filtration and the lyophilized product (FIG. 1c). This suggests that the above purification processes inhibit a drop in purity of vancomycin.

EXAMPLE 2

Reverse Osmosis Filtration

First, 250 g of the wet body obtained according to Preparation Example 1 is dissolved into 2 L of purified water, and then filtered through a 0.45 μm sterilized filter system (available from Whatman Ltd., made of cellulose nitrate, product name: disposable filter funnel). Next, purified water is added thereto to a final solution volume of 5 L. Next, the resultant solution is introduced into the sample inlet of a reverse osmosis system (available from Millipore Corporation, product name: Helicon reverse osmosis system, membrane: Nanomax™ 50 membrane), and then concentrated while maintaining the pressure at 8 bars. After the solution is concentrated until about 3 L of filtrate is obtained, 3 L of purified water is added. Next, the solution is further concentrated by applying the same pressure until 3 L of filtrate is obtained, 3 L of purified water is further added to, and the solution is further concentrated to a final volume of about 0.5 L. Then, the system is depressurized and the resultant concentrate is recovered for 10 minutes.

After analyzing the recovered concentrate, it is shown that vancomycin has a purity of 96.4%, a concentration of 142 g/L and an ethanol content of 0.24% (w/v).

Lyophilization

The vancomycin concentrate having a concentration of 142 g/L is poured into a container made of iron to a level of 1 cm of lower, and lyophilized completely at −70° C. for 1 day. Next, the iron container containing the lyophilized concentrate is introduced into a lyophilization system (available from Labconco, product name: Freeze dry system), the shelf temperature of which is controlled to −40° C., and lyophilized for 42 hours. The lyophilized vancomycin is analyzed.

It is shown from the analysis that there is no change in vancomycin purity (96.4%) 24 hours after the lyophilization, and the ethanol content and the moisture content are 0.11% (w/v) and 2.7% (w/v), respectively.

EXAMPLE 3

Reverse Osmosis Filtration

First, 290 g of the wet body obtained according to Preparation Example 2 is dissolved into 2 L of purified water, and then filtered through a 0.45 μm sterilized filter system (available from Whatman Ltd., made of cellulose nitrate, product name: disposable filter funnel). Next, purified water is added thereto to a final solution volume of 6 L. Next, the resultant solution is introduced into the sample inlet of a reverse osmosis system (available from Millipore Corporation, product name: Helicon reverse osmosis system, membrane: Nanomax™ 50 membrane), and then concentrated while maintaining the pressure at 8 bars. After the solution is concentrated until about 3 L of filtrate is obtained, 3 L of purified water is added. Next, the solution is further concentrated by applying the same pressure until 3 L of filtrate is obtained, 3 L of purified water is further added to, and the solution is further concentrated to a final volume of about 0.5 L. Then, the system is depressurized and the resultant concentrate is recovered for 10 minutes.

After analyzing the recovered concentrate, it is shown that vancomycin has a purity of 96.0%, a concentration of 176 g/L and an ethanol content of 0.22% (w/v).

Lyophilization

The vancomycin concentrate having a concentration of 176 g/L is poured into a container made of iron to a level of 1 cm of lower, and lyophilized completely at −70° C. for 1 day. Next, the iron container containing the lyophilized concentrate is introduced into a lyophilization system (available from Labconco, product name: Freeze dry system), the shelf temperature of which is controlled to −40° C., and lyophilized for 42 hours. The lyophilized vancomycin is analyzed.

It is shown from the analysis that there is little change in vancomycin purity (95.8%) 24 hours after the lyophilization, and the ethanol content and the moisture content are 0.18% (w/v) and 3.0% (w/v), respectively.

EXAMPLE 4

Reverse Osmosis Filtration

First, 274 g of the wet body obtained according to Preparation Example 2 is dissolved into 2 L of purified water, and then filtered through a 0.45 μm sterilized filter system (available from Whatman Ltd., made of cellulose nitrate, product name: disposable filter funnel). Next, purified water is added thereto to a final solution volume of 6 L. Next, the resultant solution is introduced into the sample inlet of a reverse osmosis system (available from Millipore Corporation, product name: Helicon reverse osmosis system, membrane: Nanomax™ 50 membrane), and then concentrated while maintaining the pressure at 8 bars. After the solution is concentrated until about 3 L of filtrate is obtained, 3 L of purified water is added. Next, the solution is further concentrated by applying the same pressure until 3 L of filtrate is obtained, 3 L of purified water is further added to, and the solution is further concentrated to a final volume of about 0.5 L. Then, the system is depressurized and the resultant concentrate is recovered for 10 minutes.

After analyzing the recovered concentrate, it is shown that vancomycin has a purity of 96.0%, a concentration of 162 g/L and an ethanol content of 0.09% (w/v).

Lyophilization

The vancomycin concentrate having a concentration of 162 g/L is poured into a container made of iron to a level of 1 cm of lower, and lyophilized completely at −70° C. for 1 day. Next, the iron container containing the lyophilized concentrate is introduced into a lyophilization system (available from Labconco, product name: Freeze dry system), the shelf temperature of which is controlled to −40° C., and lyophilized for 42 hours. The lyophilized vancomycin is analyzed.

It is shown from the analysis that there is little change in vancomycin purity (96.0%) 24 hours after the lyophilization, and the ethanol content and the moisture content are 0.08% (w/v) and 3.1% (w/v), respectively.

Figure 2:
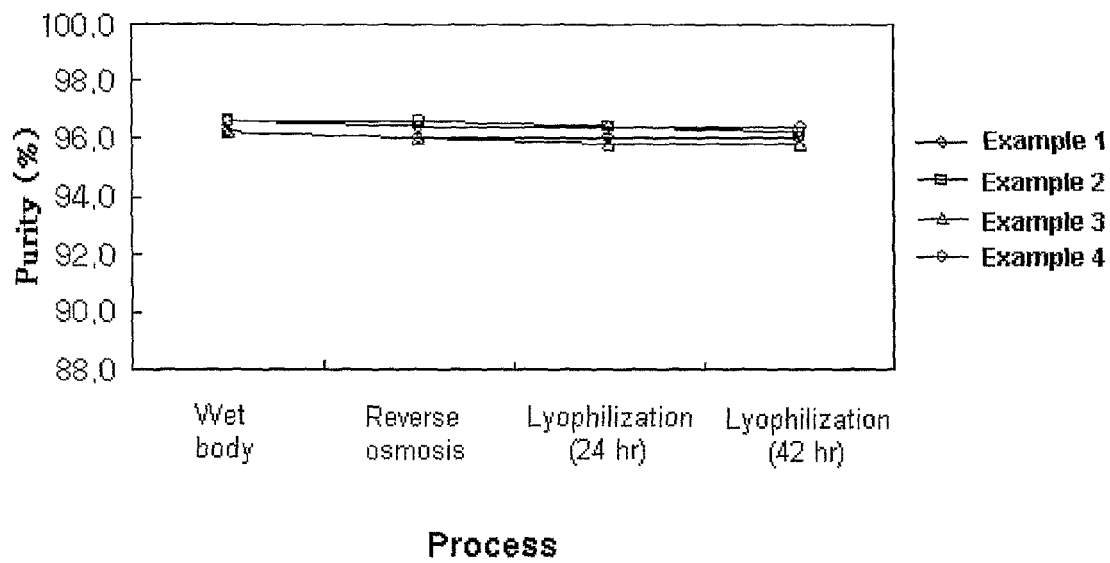
FIG. 2 is a graph showing a change in purity of vancomycin during the purification process of a vancomycin-containing wet body according to Examples 1-4.

FIG. 2 is a graph showing a change in purity of vancomycin during the purification process of a vancomycin-containing wet body according to Examples 1-4. As can be seen from FIG. 2, the purity of vancomycin is maintained constantly without any significant degradation during the purification process according to the present invention.

COMPARATIVE EXAMPLE 1

Figure 3:
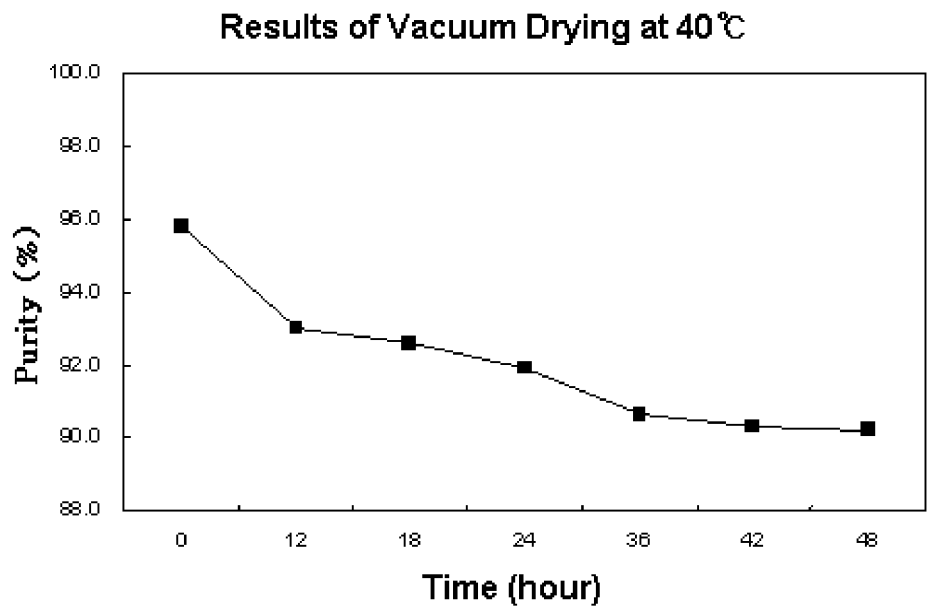
FIG. 3 is a graph showing a change in purity of vancomycin during the purification process of a vancomycin-containing wet body according to Comparative Example 1.

Dried vancomycin is obtained according to U.S. Pat. No. 7,018,814 and Korean Patent No. 554481. In other words, 50 g of the wet body obtained from Preparation Example 3 is vacuum dried at 40° C. for 48 hours. As can be seen from FIG. 3, vancomycin has a purity of 93.0%, 12 hours after the vacuum drying; 92.8%, 18 hours after the vacuum drying; 91.9%, 24 hours after the vacuum drying; 90.6%, 36 hours after the vacuum drying; 90.3%, 42 hours after the vacuum drying; and 90.2%, 48 hours after the vacuum drying. During the 2-day vacuum drying process, ethanol content and moisture content are 0.09% and 2.9%, respectively. It can be seen from the above results that the vacuum drying may not be applicable to purification of vancomycin in practice, due to a drop in vancomycin purity of at least about 5% during the 2-day vacuum drying process.

COMPARATIVE EXAMPLE 2

Comparative Example 1 is repeated, except that the vacuum drying is carried out at 25° C. for 5 days. After the vacuum drying, it is shown that vancomycin purity is 94.6%, ethanol content is 0.6% (w/v) and moisture content is 8% (w/v), which cannot satisfy the European Pharmaceutical Standards.

COMPARATIVE EXAMPLE 3

Dried vancomycin is obtained according to the method as disclosed in U.S. Pat. No. 5,853,720. In other words, 69.7 g of the wet body obtained according to Preparation Example 4 is dissolved into purified water to a final volume of 200 ml, the concentration is adjusted to 150 g/L, and then dried by using a spray drier (available from BUCHI, product name: Mini spray drier B-191). To perform the spray drying, the inlet temperature and the outlet temperature are set to 130° C. and 85° C., respectively. The sample is introduced at a flow rate of 5 ml/min.

Figure 4:
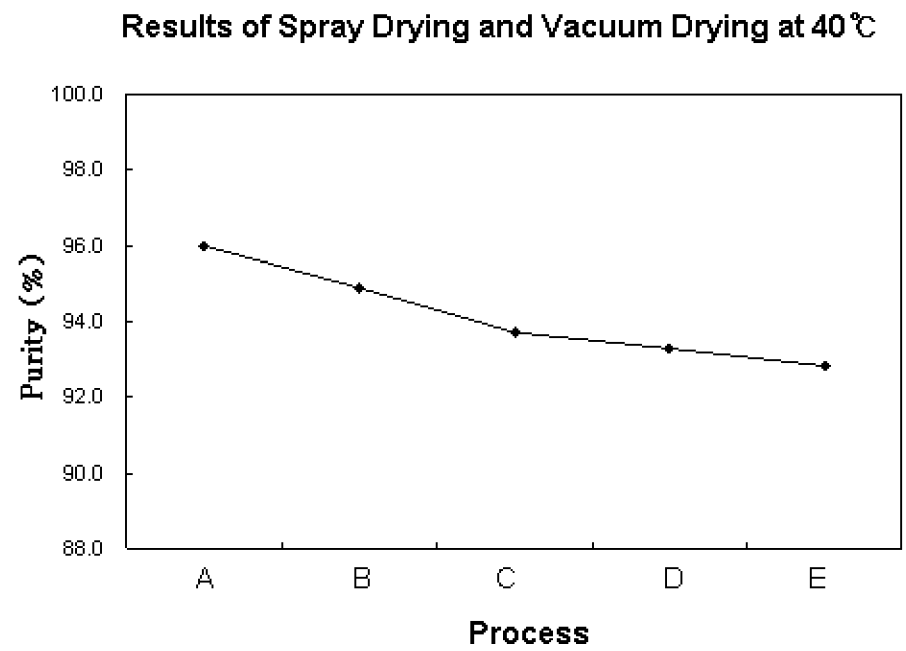
FIG. 4 is a graph showing a change in purity of vancomycin during the purification process of a vancomycin-containing wet body according to Comparative Example 3.

After the spray drying, it is shown that vancomycin purity is 94.9% and moisture content is 8.6% (w/v). The spray dried sample is recovered and vacuum dried at 40° C. for 2 days. As can be seen from FIG. 4, vancomycin purity is 93.7% (C), 12 hours after the vacuum drying, 93.3% (D), 36 hours after the vacuum drying, and 92.8% (E), 48 hours after the vacuum drying. In addition, 48 hours after the vacuum drying, moisture content is 4.6% (w/v). Therefore, such spray drying and vacuum drying cause a drop in purity of at least 3%. Moreover, it is thought that an ethanol content of 0.2% (w/v) and a moisture content of about 5% (w/v), similar to the standard value, limit preparation of stable high-purity vancomycin.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A process for purifying vancomycin, comprising:
   dissolving a wet body obtained from a microorganism-fermented solution containing vancomycin into a water soluble solvent to a concentration of about 1 to about 40 g/L, wherein said wet body has a moisture content of 30 to 50% (w/v) and vancomycin in the wet body has a purity of 93% or higher;
   carrying out reverse osmosis filtration to concentrate said vancomycin to a concentration of about 50~200 g/L which results in a purity of about 95% or higher; and
   carrying out lyophilization of the filtered vancomycin wherein the purity of said vancomycin changes less than 1% during said lyophilization.

2. The process for purifying vancomycin according to claim 1, wherein the water soluble solvent is water, a C1-C4 aliphatic alcohol or mixture thereof.

3. The process for purifying vancomycin according to claim 1, wherein the reverse osmosis filtration uses a membrane having a cut-off molecular weight of about 100 Da to about 500 Da.

4. The process for purifying vancomycin according to claim 1, wherein the vancomycin filtered by the reverse osmosis filtration has an ethanol content less than 0.5% (w/v).

5. The process for purifying vancomycin according to claim 1, wherein the lyophilization comprises:
   freezing the filtered vancomycin at −4° C. to −196° C. for about 3 to about 48 hours; and
   lyophilizing the frozen vancomycin in a freeze drier at about −60° C. up to about 40° C. for about 12 to about 48 hours.

6. The process for purifying vancomycin according to claim 1, wherein the lyophilized vancomycin has an ethanol content less than 0.3% (w/v).

7. The process for purifying vancomycin according to claim 1, wherein the lyophilized vancomycin has a moisture content less than 5% (w/v).

* * * * *